United States Patent [19]

Graham

[11] 4,380,169

[45] Apr. 19, 1983

[54] METHOD AND APPARATUS FOR MEASURING MOISTURE TENSION IN LEAVES OF GROWING PLANTS

[75] Inventor: Ellis R. Graham, Columbia, Mo.

[73] Assignee: The Curators of the University of Missouri, Columbia, Mo.

[21] Appl. No.: 226,765

[22] Filed: Jan. 21, 1981

[51] Int. Cl.³ .................................. G01N 21/00
[52] U.S. Cl. ........................................... 73/73
[58] Field of Search .................. 73/73; 250/338, 339, 250/351

[56] References Cited

U.S. PATENT DOCUMENTS 3,405,268  10/1968  Brunton ........................... 250/339
3,851,175  11/1974  Dahlin et al. ..................... 250/339
4,069,716  1/1978  Vanasco et al. .................. 73/73 X

FOREIGN PATENT DOCUMENTS 1315435  12/1962  France ............................... 73/73

Primary Examiner—Herbert Goldstein
Attorney, Agent, or Firm—Ray E. Snyder

[57] ABSTRACT

A method and apparatus to measure moisture tension in a leaf of a growing plant is described. The apparatus includes a pair of separable jaws for clamping a leaf between a standard light source and a photoelectric detector which are connected electrically to a regulated bias network and through an analog-to-digital converter panel meter. The measurement appearing on the readout is compared with a predetermined calibration source. The instrument as a whole is called a Moisture Tension Radiometer.

2 Claims, 5 Drawing Figures

METHOD AND APPARATUS FOR MEASURING MOISTURE TENSION IN LEAVES OF GROWING PLANTS

BACKGROUND OF THE INVENTION

1. Field of the Invention

This invention relates to the field of measuring and testing, and more particularly to apparatus for the testing of moisture tension in the leaves of growing plants. The invention is directed to the measurement directly of moisture tension in living plants, as opposed to the measurement of total moisture content, or measurement of soil moisture content.

Moisture tension may be defined as the equivalent negative pressure in plant water which is equal to the equivalent pressure that must be applied to the plant water to bring it to hydraulic equilibrium.

2. Description of Prior Art

The measurement of the moisture tension in a growing plant can be a useful indicator of plant stress and other factors that may affect the optimum growing conditions for the plant. It is known that the moisture tension in a plant can vary due to a number of factors, such as the time of day, the amount of photosynthesis taking place within the plant, the ambient relative humidity, and the soil moisture content.

A method for determining moisture tension in plants using air pressure in a sealed system has been described by Dr. Sholander in Science, Vol. 148, pgs. 339–346 (1965). In this system a plant is cut and placed within a pressure vessel. As the air pressure within the vessel increases, the plant sap accumulates on the cut stem. The air pressure at which the plant sap flows is considered the moisture tension and is expressed in atmospheres, sometimes called the negative leaf potential. The vessel in the system described by Dr. Sholander utilizes relatively high pressure and is relatively expensive and dangerous. The procedure is time consuming and also requires that the plant be cut to be placed within the vessel. The instrument of the present invention is intended to measure moisture tension directly in living plants without harming the plant in any way.

A large number of instruments have been described in the patent art for the measurement and testing of non-electrical properties such as moisture. These instruments generally rely upon changes in capacity or resistance due to the presence of moisture. Examples of such patents for the measurement of the moisture content of paper are U.S. Pat. Nos. 2,873,605 and 2,947,166.

Photoelectric instruments have also been used in a wide variety of applications and are known for use in the measurement of moisture content of a vapor stream, for example in U.S. Pat. No. 1,924,139.

There have also been developed a number of instruments for measuring the moisture content of the soil surrounding growing plants, as for example in U.S. Pat. No. 3,951,098. Such devices have also been used in conjunction with automatic irrigation control systems as shown in U.S. Pat. No. 3,910,300.

SUMMARY OF THE INVENTION

It is an object of the present invention to provide an improved, inexpensive instrument for the measurement directly of moisture tension in a living plant. The measurement is accomplished by placing a leaf between a standard light source and a photoelectric detector and calibrating the light transmitted through the leaf. The photoelectric detector is connected to a digital panel display to indicate the intensity of the light transmitted.

It is a more particular object to provide an instrument of the type described that is portable, precise in its accuracy, reasonable in cost and which can make the desired measurements within 4 to 5 seconds.

It is a more particular object to provide an instrument of the type described that is capable of making the measurement of moisture tension in a manner that is not destructive to any part of the plant.

It is an additional object to provide an instrument for measuring moisture tension that can be integrated into a control system for determining the best time to irrigate crops so as to produce the highest yields obtainable for the amount of water used.

DESCRIPTION OF THE PREFERRED EMBODIMENT

Figure 1:
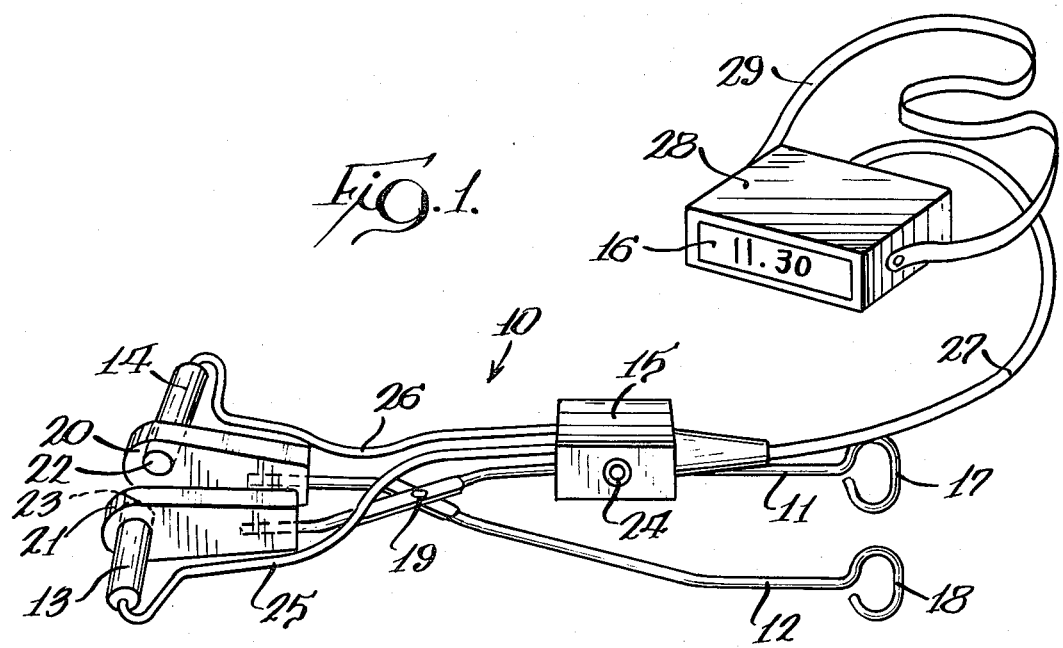
FIG. 1 is a perspective view of an embodiment of the radiometer of the present invention.

The instrument of the present invention, herein called a Moisture Tension Radiometer, is illustrated in FIG. 1 and is designated as a whole by the numeral 10. The radiometer 10 comprises a pair of manually operable pivoted arms 11 and 12, a standard light source 13, a photoelectric detector 14, a switch box 15 and a liquid crystal digital readout 16. The arms 11 and 12 have handles 17 and 18 respectively and are pivotally connected together at 19. Mounting blades 20 and 21 are attached to the free ends of the arms 12 and 11, respectively. The standard light source 15 is mounted on the blade 20. The blades 20 and 21 are formed with apertures 22 and 23 respectively which are brought into coincidence when blades 20 and 21 are clamped together by actuation of the handles 17 and 18.

The switch box 15 is shown as mounted on the arm 11 and has a manually actuable switch 24. The switch box 15 is connected to the light source 13 by a lead 25 and to the photo detector 14 by a lead 26. The switch box 15 is also connected by means of a lead 27 to the readout display 16. the liquid crystal display 16 may be contained within a box or housing 28 which may have a carrying strap 29 adapted to be worn around the neck of the operator.

In operation, the radiometer is utilized as follows:

The handles 17 and 18 are squeezed together by an operator bringing the blades 20 and 21 into coincident without a leaf being present. The switch 24 is actuated as to determine the initial light intensity transmitted from the light source 13 and as measured by the detector 14. The magnitude of this intensity is indicated on the display 16.

The arms 11 and 12 are then opened and a leaf placed between the blades 20 and 21. The arms 11 and 12 are again squeezed together clamping the leaf between the light source 13 and the detector 14. The switch 24 is again closed and the intensity of the light transmitted through the leaf and as measured by the detector 14 is indicated on the display 16. This measurement will be significantly lower than the initial intensity.

The adsorption co-efficient ($\mu$) may now be determined by the following formula:

$$\mu = \ln I_o - \ln I/d$$

Where:
$I_o$ is the initial intensity;
I is the intensity of light transmitted through the leaf; and
d is the mean leaf thickness in centimeters.

Figure 4:
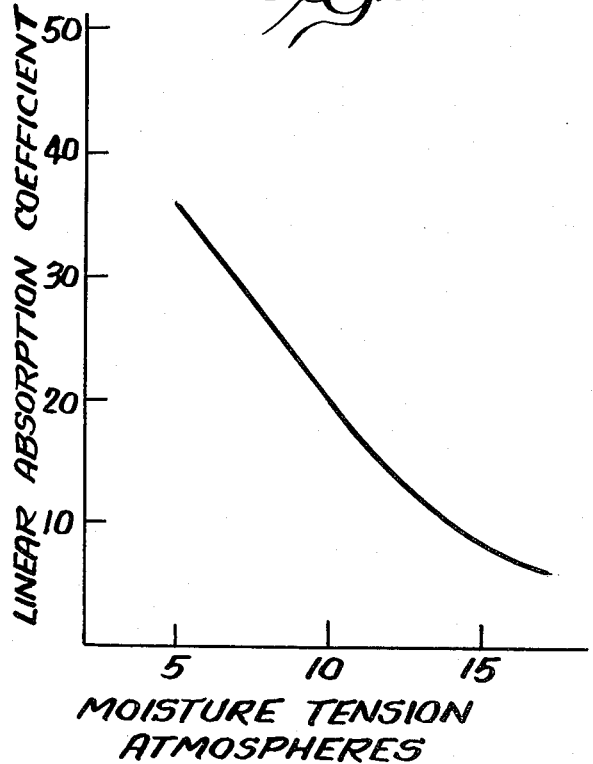
FIG. 4 is a graph showing the relation of the adsorption co-efficient ($\mu$) as measured by the radiometer to the moisture tension of a soybean leaf as measured by the Sholander bomb method.
Figure 5:
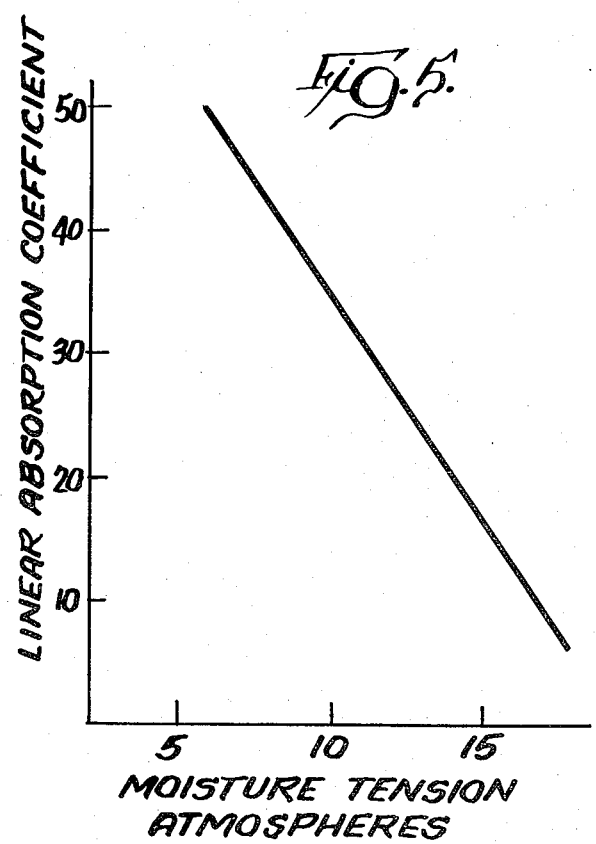
FIG. 5 is a graph showing the relation of the adsorption co-efficient ($\mu$) as measured by the instrument of the present invention of the moisture tension of corn leaves as measured by the Sholander bomb method.

Once this value is obtained the moisture tension of the leaf can be obtained from a calibration curve for the plant species of interest as shown in FIGS. 4 and 5.

Figure 2:
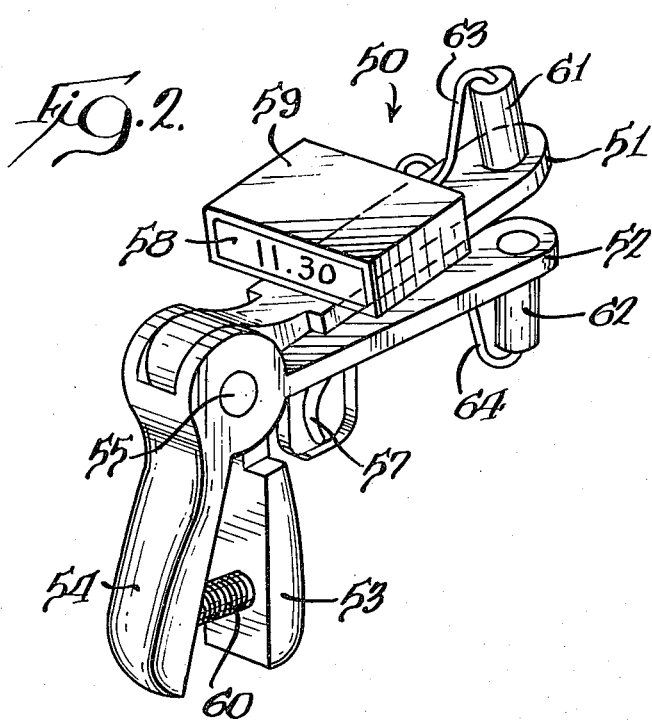
FIG. 2 is a perspective view of a modified embodiment of the radiometer designed for one hand operation.

Referring now to FIG. 2 there is illustrated an alternative embodiment of the invention designed for one hand operation. The radiometer of FIG. 2 is designated as a whole by the numeral 50 and comprises a pair of blades or jaws 51 and 52 attached to integral handles 53 and 54, respectively. The handles 53 and 54 are generally of a pistol grip appearance and are pivoted together by a pin 55. A spring 56 is disposed between the grips 53 and 54 so as to maintain the blades 51 and 52 in a normally open position. A trigger actuated switch 57 is mounted beneath the blade 52 and a liquid crystal display 58 is contained within a box 59 mounted on top of the blade 51. A light source 61 is carried by the blade 51 and a photo detector 62 is carried by the blade 52. The light source 61 is connected to the switch 57 by a lead 63 and the photo detector 62 is connected to the display by a lead 64.

The radiometer 50 is operated in substantially the same manner as described for the radiometer 10 except that the end grips 53 and 54 are easily retained within one hand for the operator and the switch 56 is actuated by one finger of the same hand.

Figure 3:
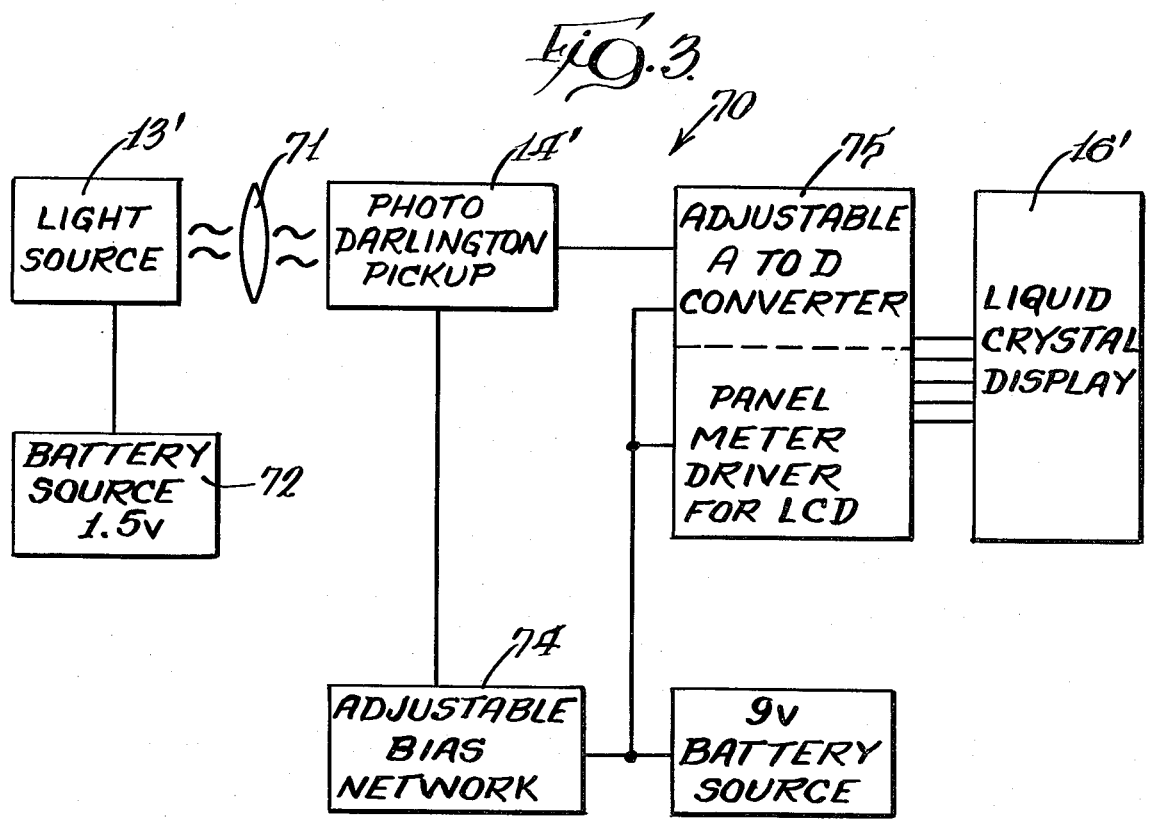
FIG. 3 is a schematic block diagram of the electrical circuit incorporated in the invention.

Referring now to FIG. 3 there is illustrated the schematic block diagram of the electronic portion of the invention. The circuit as a whole is designated by the numeral 70 and comprises the light source 13', the photo detector 14' and the liquid crystal display 16'. A focusing lens 71 is interposed between the light source 13' and detector 14'. The light source 13' is powered by a battery source 72. The photoelectric detector 14' may be connected to a battery source 73 through an adjustable bias network 74. The photo detector 14' is also connected to a liquid crystal display 16' through a converter 75. The converter 75 includes an analog to digital converter and a panel meter driver for the liquid crystal display 16'.

In an experimental model of the present invention liquid crystal display was calibrated to provide an initial four digit reading of 1990±9. This was the initial reading corresponding to the light intensity as measured directly from the standard lamp source. The reading whenever a leaf is interposed between the light source and the photo detector is lower depending upon the optical density of the particular leaf. The optical density has been found to vary with the moisture tension in the leaf. This measurement of moisture tension also has been found to correlate with the observation of soil water differences in irrigated and non-irrigated plots. This radiometer has also established that moisture tension of plant leaves can be measured accurately by determining the rate of transmitted light.

It is contemplated that an instrument of this type might be incorporated into a complete irrigation system through a suitable control system so as to provide irrigation water only when needed and only in the amounts needed so as to maximize the yield from the plants for a given amount of water.

The measurements as made and appearing on the digital readout are compared with a standardized calibration curve for the particular variety of plant as shown in FIGS. 4 and 5. It is contemplated that a comparable curve or a comparable set of data for the particular plant species could be incorporated as part of the liquid crystal display so as to provide a direct and immediate comparison.

It is to be understood that the embodiments shown and described are the preferred ones and that many changes and modifications may be made thereto without departing from the spirit of the invention. The invention is not to be considered as limited to these embodiments except insofar as the claims may be so limited.

I claim:

1. A method for measuring moisture tension in a leaf of a growing plant by means of an instrument having a pair of separable jaws with a standard light source mounted on one jaw and a photoelectric detector mounted on the other jaw, with both connected to a digital panel meter, the steps comprising:
   initially squeezing the jaws together, without a leaf present, to bring the light source into coincidence with the detector to establish an initial intensity of light transmitted to the detector and display on the meter;
   placing a leaf between the jaws and squeezing said jaws together to measure the light intensity transmitted through said leaf and displayed on said meter; and
   comparing the measurements made with some predetermined standard measurements for the particular plant leaf of interest.

2. An instrument for measuring directly the moisture tension in a leaf of a growing plant comprising:
   a pair of moveable separable jaws adapted to engage a plant leaf by moving said jaws together;
   a standard light source mounted on one of said jaws;
   a photoelectric detector mounted on the other of said jaws and adapted to be actuated by light from said source when said jaws are close;
   an electrically operated digital display connected to said detector and adapted to provide a readout corresponding to the intensity of light transmitted from said source to said detector;
   an electrical power source connected to said light source and to said detector and to said display for energizing same;
   switch means for connecting said power source to said light source and simultaneously energizing said detector and said display; and
   means for comparing the intensity of light detected by said detector with a predetermined standard for a particular plant species being measured.

* * * * *